(12) United States Patent
De Jonge et al.

(10) Patent No.: US 7,299,145 B2
(45) Date of Patent: *Nov. 20, 2007

(54) METHOD FOR THE AUTOMATIC SIMULTANEOUS SYNCHRONIZATION, CALIBRATION AND QUALIFICATION OF A NON-CONTACT PROBE

(75) Inventors: Lieven De Jonge, Overijse (BE); Bart Van Coppenolle, Linden (BE); Denis Vanderstraeten, Louvain-la-Neuve (BE)

(73) Assignee: Metris N.V., Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/486,370

(22) Filed: Jul. 14, 2006

(65) Prior Publication Data

US 2007/0043526 A1 Feb. 22, 2007

Related U.S. Application Data

(60) Provisional application No. 60/708,371, filed on Aug. 16, 2005.

(30) Foreign Application Priority Data

Aug. 16, 2005 (EP) .................................. 05447188

(51) Int. Cl.
G01B 11/24 (2006.01)

(52) U.S. Cl. .......................... 702/104; 702/91; 702/94; 702/152; 702/167; 356/601

(58) Field of Classification Search ................ 702/104, 702/105, 91, 94, 95, 150, 152, 167; 600/300, 600/428; 356/153, 601
See application file for complete search history.

(56) References Cited

U.S. PATENT DOCUMENTS

| 6,493,956 | B1* | 12/2002 | Matsuda ...................... 33/502 |
| 6,583,869 | B1* | 6/2003 | Sheridan ..................... 356/153 |
| 6,944,564 | B2 | 9/2005 | De Jonge |
| 2004/0024311 | A1* | 2/2004 | Quaid, III .................... 600/428 |
| 2004/0034282 | A1* | 2/2004 | Quaid, III .................... 600/300 |

FOREIGN PATENT DOCUMENTS

| EP | 1 361 414 A1 | 11/2003 |
| JP | 2000180103 A * | 6/2000 |

(Continued)

OTHER PUBLICATIONS

European Search Report dated Dec. 20, 2005, issued in connection with corresponding EP 05 44 7188.

(Continued)

*Primary Examiner*—Carol S. W. Tsai
(74) *Attorney, Agent, or Firm*—Nixon & Vanderhye P.C.

(57) ABSTRACT

The present invention relates to an improved method for the simultaneous calibration and qualification of a non-contact probe on a localizer using a single artifact, in which non-contact probe readings and localizer readings are synchronised using parameters determined simultaneously with calibration and qualification. The invention also relates to a non-contact probe and other devices, and a computer program for performing the invention.

26 Claims, 2 Drawing Sheets

```
void CalibrateAndQualify(in Pr, in M, out N, out Q, out s)
{
    // Initialization (set to zero)
    N = 0;
    Q = 0;
    C = 1e100;
    s = 0 ;
    for iter = 1 to 10000
    {
        // Perturb the current nurbs
        for i = 1 to nc
            Nnew(i) = N(i) + rand(-1,1);
        // Perturb the current orientation
        for i = 1 to 6
            Qnew(i) = Q(i) + rand(-1,1);
        // Perturb the current synchronization
        for i = 1 to nv
            snew(i) = s(i) + rand(-1,1);
        // Compute the 3D points
        for i = 1 to n
            P3(i) = Eval(Pr(i), Nnew, Qnew, M, s);
        // Fit the points to the artifact
        Cnew = Fit(P3);
        // Update the best calibration/qualification so far
        if (Cnew < C)
        {
            C = Cnew;
            N = Nnew;
            Q = Qnew;
            s = snew;
        }
        // Stop if necessary
        if (C < tol)
            return;
    }
}
////////////////////////////////////////////////////////////
////////////

Point3D Eval(in Pr, in N, in Q, in M, in s)
{
    // Nurbs evaluation see Piegl&Tiller
    P = N(Pr);
    // Nurbs evaluation of the time
    t = s(Pr);
    // Orientation where Q is q 4x4 matrix
    P = Q*P;
    // Machine position using any interpolation technique
    m = M(t);
    // Point relative to the object
    P = P + m;
    return P;
}
////////////////////////////////////////////////////////////
////////////
double Fit(in P)
{
    // Fit the artifact (here a sphere is taken as example)
    S = FitSphere(P, radius, center);
    // Compute the cost
    C = 0;
    for i = 1 to n
        C = C + abs((center-P(i))^2-radius^2);
    return C;
}
```

FOREIGN PATENT DOCUMENTS

| | | |
|---|---|---|
| WO | WO 00/39522 | 7/2000 |
| WO | WO 00/41141 | 7/2000 |
| WO | WO 200039522 A1 * | 7/2000 |
| WO | WO 01/07866 | 2/2001 |
| WO | WO 200107866 * | 2/2001 |

OTHER PUBLICATIONS

Patent Abstracts of Japan, vol. 2000, No. 9, Oct. 13, 2000 & JP 2000 180103.

File History of U.S. Patent No. 6,944,564 obtained from PTO IFW Jun. 20, 2007.

* cited by examiner

FIGURE 1-1

```
void CalibrateAndQualify(in Pr, in M, out N, out Q, out s)
{
      // Initialization (set to zero)
      N = 0;
      Q = 0;
      C = 1e100;
      s = 0 ;

for iter = 1 to 10000
      {
            // Perturb the current nurbs
            for i = 1 to nc
                  Nnew(i) = N(i) + rand(-1,1);

// Perturb the current orientation
            for i = 1 to 6
                  Qnew(i) = Q(i) + rand(-1,1);

// Perturb the current synchronization
            for i = 1 to nv
                  snew(i) = s(i) + rand(-1,1);

// Compute the 3D points
            for i = 1 to n
                  P3(i) = Eval(Pr(i), Nnew, Qnew, M, s);

// Fit the points to the artifact
            Cnew = Fit(P3);

// Update the best calibration/qualification so far
            if (Cnew < C)
            {
                  C = Cnew
                  N = Nnew;
                  Q = Qnew;
                  s = snew;
            }

// Stop if necessary
            if (C < tol)
                  return;
      }
}
/////////////////////////////////////////////////////////////
//////////
```

FIGURE 1-2

```
Point3D Eval(in Pr, in N, in Q, in M, in s)
{
      // Nurbs evaluation see Piegl&Tiller
      P = N(Pr);

// Nurbs evaluation of the time
      t = s(Pr);

// Orientation where Q is q 4x4 matrix
      P = Q*P;

// Machine position using any interpolation technique
      m = M(t)

// Point relative to the object
      P = P + m;

return P;
}

////////////////////////////////////////////////////////////////
////////// double Fit(in P)
{
      // Fit the artifact (here a sphere is taken as example);
      S = FitSphere(P, radius, center);

// Compute the cost
      C = 0;
      for i = 1 to n
            C = C + abs((center-P(i))^2-radius^2);

return C;
}
```

METHOD FOR THE AUTOMATIC SIMULTANEOUS SYNCHRONIZATION, CALIBRATION AND QUALIFICATION OF A NON-CONTACT PROBE

This application claims benefit of EP 05447188.3, filed 16 Aug. 2005, and U.S. Provisional Application No. 60/708,371 filed 16 Aug. 2005, the entire contents of each of which are hereby incorporated by reference.

FIELD OF THE INVENTION

The present invention relates to a method for the calibration, qualification and synchronization of a non-contact probe on a localizer in a single step procedure, using a single reference object, in which synchronization, calibration and qualification are performed simultaneously.

BACKGROUND OF THE INVENTION

Generally a non-contact probe comprises of one or more emitter sources and one or more receivers. An emitter source projects waves, for example light waves, on the object of interest; the receiver(s) comprising for example a camera, capture(s) the returning waves from the object. For instance, if the receiver is a CCD-camera, it will take one or more shots of the object. By moving the object relative to the non-contact probe or vice versa, shots of the complete object can be taken, i.e. the object is being scanned. Each shot represents a one-dimensional (1D), two-dimensional (2D) or three-dimensional (3D) projection of the object depending on the physical form and working principle of the receiver(s). To obtain accurate 3D points on the surface of the object, relative to a fixed coordinate system, from multiple shots the following system parameters are preferably required:
1. the 3D position of the emitter source(s) relative to the receiver(s);
2. the 3D position and orientation of the emitted waves, relative to the receiver(s), coming from the emitter source(s);
3. the characteristics such as focal point of lenses of the receivers used in the non-contact probe;
4. the dimensions and measuring resolution of the receiver(s); and
5. the 3D position and orientation of the non-contact probe or the object relative to a fixed coordinate system, for each receiver capture.

The actual values of the parameters 1 to 4 are calculated during the calibration. Some of the actual values of parameter 5 are calculated during the qualification procedure, others are given values readily obtainable from the object-non-contact probe set-up. When these parameters are calculated for the given non-contact probe, the conversion, also called compensation, from receiver readings to accurate 3D points can be performed.

To be able to move the non-contact probe relative to the object, the probe is mounted on a localizer. This localizer can be a structure, portable or non-portable, on which the probe is mounted, like for example a tripod. This localizer can also be a structure with moving axes, motorized or non-motorized, where the probe is mounted on the end of said axes, dependent to all other axes, like for example a robot, a milling machine or coordinate measuring machine (CMM). These last types of localizer can have the possibility to record the position and/or the rotation of the probe.

Some of the state-of-the-art techniques actually calculate parameters 1 to 5 explicitly using dedicated measurements in a sequential manner. Adjusting these parameters is difficult because of their complex interactions and adjustment can be time consuming.

Other state-of-the-art techniques for calibration and qualification do not calculate these parameters explicitly. In the first step, the receiver readings are first transformed in one, two or three dimensions, depending on whether the receiver itself is capable of measuring one, two or three dimensions. In this calibration step a receiver reading in receiver units is transformed to a point in e.g. SI units. The calibration can take several phenomena into account; for example, correcting the perspective since the object is not always parallel to the receiver or scaling correctly the readings. Finally, it must model correctly systematic reading errors in the receiver (s)—which is a complex operation.

The second step, the qualification, consists of determining the accurate position and orientation of the non-contact probe relative to a fixed coordinate system. The qualification procedure is generally performed by the end-user using special artifacts or other measuring equipment. The qualification procedure often requires an essential manual alignment of the artifact/measuring equipment with the non-contact probe.

Both steps, calibration and qualification, are based on some parameters that are tuned or optimized to obtain the 3D points accurately. Most state of the art algorithms determine the values of the parameters for the two steps separately, usually scanning different artifacts with known features, dimensions, etc. A method to generate the parameters with an integrated approach using one single artifact and a general function to convert directly a receiver reading into a three dimensional point has been recently disclosed (EP 1 361 414). This function corresponds to a sequence of calibration and qualification and, therefore, depends on many parameters similar to the ones used in the classical de-coupled technique. By expressing the conversion with one function, all interactions between the parameters are considered. Also, if the object being measured is known, the influence of a single parameter can directly be measured in terms of accuracy of the resulting 3D point.

Measurement using such technique relies on accurate determination of the probe position and/or orientation by the localiser for a given probe reading. Any error or lack of accuracy leads to a less precise calibration and qualification, and consequently costly readjustment. When taking measurements, the frequency of the receiver readings and the frequency of localizer readings rarely match or, the frequencies match but the phases are different. For example, a continuously moving probe may generate a high number of probe readings during movement, but this may not be matched by the same number of localizer readings in a given time period. Alternatively, the same numbers of readings are performed but a delay occurs. The difference is due to incompatibility between the electronics of the detector and localizer which are not synchronised. The result is that for each receiver reading there is commonly no corresponding localizer reading. The accuracy and precision of the calibration is consequently reduced. To overcome the problem, the electronic circuitry of both the detector and the localizer may be adapted to provide reading information at the same frequency and in synchronization. However, the adapted circuitry must be specialised and bespoke according to the output type of the respective devices. Should the same localizer be used with several different probes, electronic synchronization would entail a corresponding number of sets of adapted circuitry, so increasing costs. In more complex situations, a receiver obtains multiple readings in a periodic manner, each reading provided with a time stamp but the precise time stamp of each reading in one cycle cannot be synchronised. The synchronization with the localizer data cannot even be obtained with adapting hardware circuitry.

The present invention provides an adaptation to the technique described in (EP 1 361 414). It overcomes the problem of asynchronous data in the probe and localizer by mathematically identifying the time stamp of every receiver reading using a synchronization model with a few parameters and interpolating the corresponding localiser data for this time stamp. The parameters of the synchronization model are computed simultaneously during calibration and qualification.

BRIEF DESCRIPTION OF THE FIGURE

FIG. 1. An example of an algorithm according to the invention incorporating synchronization. Pr is the array of receiver data (size n), M is the corresponding machine positions (size n), N is the array of control points of the NURBS (size nc), and Q is the qualification matrix (size 6), s is the synchronization matrix.

SUMMARY OF THE INVENTION

One embodiment of the present invention is a method for the calibration, qualification and synchronization of a point cloud generator, said point cloud generator comprising a non-contact probe on a localizer, comprising determining the transformation of an electrical reading of the receivers in said non-contact probe in point coordinates relative to said probe and identifying the position and orientation of the said non-contact probe in the measuring volume of the said localizer, thereby determining calibration, qualification and synchronization parameters simultaneously.

Another embodiment of the present invention is a method as described above whereby calibration, qualification and synchronization are performed using the same artifact.

Another embodiment of the present invention is a method as described above, whereby said artifact is a physical object susceptible to point cloud generation, whose outer shape and/or part thereof is definable using a mathematical function and/or look-up tables.

Another embodiment of the present invention is a method as described above, whereby said artifact is a sphere, cylinder or box.

Another embodiment of the present invention is a method as described above, whereby said artifact is a sphere of unknown diameter.

Another embodiment of the present invention is a method as described above, whereby said artifact has unknown dimensions prior to the execution of said method.

Another embodiment of the present invention is a method as described above, whereby said artifact has unknown position with respect to said localizer prior to the execution of said method.

Another embodiment of the present invention is a method as described above, whereby said method is performed without manual intervention.

Another embodiment of the present invention is a method as described above, whereby said method is executed at a user's site.

Another embodiment of the present invention is a method as described above, comprising the steps of:

a) scanning said artifact using said point cloud generator, b) calculating cloud points, P, using parameters relating to calibration, qualification and synchronization, c) calculating the position and optionally the orientation and/or size of said artifact using P calculated in step b) and knowledge of the artifact according to a mathematical function and/or look-up tables which define said artifact, d) comparing the values of P, with those calculated for the artifact derived from step c), e) adjusting parameters relating to calibration, qualification and synchronization, and f) repeating steps b) to e) until parameters relating to calibration, qualification synchronization are obtained which provide the closest comparison according to step d).

Another embodiment of the present invention is a method as described above whereby step b) is based on the generic function [1]

$$P=M(s(Pr))*(Q(f(Pr))+q)m(s(Pr)) \qquad [1]$$

where

Pr is a reading of a receiver of the non-contact probe,

P is a cloud point, calculated from Pr, relative to a fixed coordinate system, f is a general mapping function, that maps receiver readings to 1D, 2D or 3D point coordinates, relative to a coordinate frame fixed to the non-contact probe, Q, q are the orientation, position of the non-contact probe relative to the localizer, M, m are the orientation and position of the localizer relative to a fixed coordinate frame for a given value of Pr, s is the time stamp for a given value of Pr; all three with respect to a fixed coordinate frame; none or one or more considered as known parameters.

Another embodiment of the present invention is a method as described above wherein f is a non-uniform rational B-spline function.

Another embodiment of the present invention is a method as described above wherein s is a non-uniform rational B-spline function.

Another embodiment of the present invention is a method as described above, wherein steps b) to f) comprise:

b) calculating points according to function [1], said function re-expressed as:

$$P=F(Pr, S) \qquad [2]$$

wherein Pr is a reading of a receiver of the non-contact probe,

P is a point, calculated from Pr, relative to a fixed coordinate system,

F is a compensation function based on f, Q, q, s, M and m, said compensation function being applied to Pr using parameter set S, c) calculating the position and optionally the orientation and/or size of said artifact using the values of P obtained in step b), d) comparing the values of P, with those calculated for the artifact derived from step c), e) adjusting S, and f) repeating steps b) to e) until value of S is obtained which provides the closest comparison according to step d).

Another embodiment of the present invention is a method as described above wherein step c) comprises:

g) comparing the points P obtained in step b) to those expected of said artifact according to a mathematical function and/or look-up tables which define said artifact, h) adjusting one or more of the values corresponding to the position and optionally the orientation and/or size of said artifact, and i) repeating steps g) and h) until values corresponding to the position, and if calculated orientation and/or size are obtained which provide the closest comparison according to step g).

Another embodiment of the present invention is a method as described above wherein the values calculated for the artifact as mentioned in step d) are derived from a mathematical function and/or look-up tables which define said artifact, the values corresponding to the position, and if calculated orientation and/or size as obtained in step c).

Another embodiment of the present invention is a method as described above, wherein the comparison performed in step d) comprises one or more average square distance, variance, volume, area and/or axis of inertia calculations.

Another embodiment of the present invention is a method for the simultaneous calibration, qualification and synchronization of a point cloud generator, said point cloud generator comprising a two-dimensional line laser scanner mounted on a 2D co-ordinate measuring machine, comprising:

j) scanning a sphere using said point cloud generator, k) calculating points according to function [2]

$$P=F(Pr, S) \qquad [2]$$

wherein Pr is a reading of a receiver of the two-dimensional line laser scanner, P is a point, calculated from Pr, relative to a fixed coordinate system, F is a compensation function based on f, Q, q, s, M and m, said compensation function being applied to Pr using parameter set S, Q, q is the orientation and position of the non-contact probe relative to the localizer; M, m is the orientation position of the localizer relative to a fixed frame for a given value of Pr, both values with respect to a fixed coordinate frame and none, either or both values considered as known parameters, l) comparing the points P obtained in step k) to those expected of said sphere according to a mathematical function defining said sphere, m) adjusting one or more of the values corresponding to the position and size of said sphere, n) repeating steps l) and m) until values corresponding to the position and size are obtained which provide the closest comparison according to step l), o) comparing the values of P, with those calculated for the sphere, the latter obtained from mathematical function which defines said sphere, and the values corresponding to its position and size as obtained in step n).

p) adjusting S, and q) repeating steps k) to n) until value of S is obtained which provides the closest comparison according to step o).

Another embodiment of the present invention is a method to allow an unskilled operator to perform a calibration, qualification and synchronization of a point cloud generator, using a method as described above.

Another embodiment of the present invention is a method for performing a simultaneous calibration, qualification and synchronization of a point cloud generator within 5 minutes of generating the cloud point, using a method as described above.

Another embodiment of the present invention is a method for performing a simultaneous calibration, qualification and synchronization of a point cloud generator without manual intervention, using a method as described above.

Another embodiment of the present invention is a use of a single artifact for performing the calibration, qualification and synchronization procedure according to the method as described above.

Another embodiment of the present invention is a computer program stored on a computer readable medium, suitable for performing a method as described above.

Another embodiment of the present invention is a computer comprising a computer readable medium adapted and programmed to carry out the computer program as described above.

Another embodiment of the present invention is a non-contact probe configured to perform a method as described above.

Another embodiment of the present invention is a non-contact device comprising an artifact and a non-contact probe as described above mounted on a localizer.

DETAILED DESCRIPTION OF THE INVENTION

A "non-contact probe" can be defined as any device mounted on a localizer that through non-contact sensing conducts 1D (distance), 2D or 3D coordinates measurements.

A "localizer" is defined as any system positioning and orientating a non-contact probe in space, that returns the position and/or the orientation of the non-contact probe in 1D-, 2D- or 3D coordinates. For each position and/or orientation, the time t is given A "receiver", is an electronic device in the non-contact probe that captures the waves coming from the object to be measured, resulting in one or multiple electrical readings. Most of the time these electrical readings are voltage readings on pixels of a CCD-camera.

An "artifact" is any physical object susceptible to point cloud generation, whose outer shape and/or part thereof is definable using a mathematical function and/or look-up tables. Said artifact may be, for example, a sphere, cylinder, cube or box, two spheres joined together, a dumb-bell, a sphere joined to a cube etc. Said artifact may also be any irregular shape such as a mobile phone, a pen, a calculator etc. The method of obtaining a mathematical function and/or look-up table thereof is known to the skilled artisan. Depending on the geometry of the object, its dimensions may be known with accuracy; alternatively the dimension may not be accuracy known, or not known at all.

A "look-up table" is a data list that defines the shape and dimensions of the object.

A non-contact probe generally comprises of one or more emitter source(s), sending (e.g. light) waves to the object of interest, and one or more receivers, which capture the part of the object that is "hit" by the emitter source. The conversion of the electrical readings of the receiver to an accurate 3D point requires the steps of calibration and qualification executed on beforehand.

A "point cloud generator" is a system that comprises 2 components, namely a non-contact probe and a localizer whereby both components can be used for 1D, 2D or 3D position and/or orientation measurements.

"Calibration" is the procedure to identify the conversion between the electrical reading of the receiver in the non-contact probe and 1D, 2D or 3D point coordinates in SI units. In other words, calibration is the procedure to transform an electrical reading in accurate point coordinates.

These point coordinates are calculated relative to a coordinate system connected to the non-contact probe.

"Qualification" is defined as a procedure of completely and accurately identifying the position and orientation of the non-contact probe in the measuring volume of the localizer, possibly using information readily made available by the localizer itself. This procedure is to be performed each time the non-contact probe is mounted on the localizer or each time its position or orientation with respect to the localizer is changed. Thus, qualification is the procedure whereby the position and the orientation of the coordinate system associated with the non-contact probe is defined with respect to a fixed coordinate system.

"Synchronization" is a defined as a procedure of completely and accurately identifying the time stamp of every receiver reading.

Finally, "compensation" is defined as a procedure of making the conversion between the electrical reading of a receiver in the non-contact probe and 1D, 2D or 3D point coordinates using the calculated parameters of the calibration and qualification.

The present invention relates to a method that determines set-up parameters of a non-contact probe mounted on a localizer using only one artifact and the localizer as described in EP 1 361 414 which is incorporated herein by reference. This present method is characterized by some major improvements compared to the state-of-the-art technologies as described below. Therefore, the present method represents not only an easier but also a more time-effective method.

One aspect the present invention allows the calibration and qualification procedure to be carried out in one single step using one artifact, wherein the readings of the probe and localiser are synchronized. The present invention determines parameters pertinent to synchronization simultaneously with calibration and qualification. The simultaneous operation provides a more accurate and faster determination of the parameters, which results in a more accurate activity of the non-contact probe.

Therefore, in one embodiment, the present invention relates to a method for the calibration, qualification and synchronization of a non-contact probe comprising determining the transformation of an electrical reading of the receivers in said non-contact probe in point coordinates relative to the said probe and identifying the position and orientation of the said non-contact probe in the measuring volume of the said localizer, thereby determining calibration, qualification and synchronization parameters simultaneously.

In a one embodiment, said artifact consists of one or more spheres, cylinders, cubes or boxes, any regular or irregular physical object. According to the present invention the entire calibration-qualification-synchronization procedure can thus be totally automated; in other words there is a little or no manual interference and said procedure does not rely upon the skill of the operator. Furthermore, calibration and qualification can be performed at the user's site.

As mentioned, the calibration, qualification and synchronization steps of a non-contact probe depend on a variety of parameters. In another embodiment, the present invention relates to a method for determining the parameters of a non-contact probe in a single step using a single artifact.

The present invention is based on a general mapping function that directly converts a receiver reading into a 3D point. This function depends on various parameters that need to be numerically determined. In the following description, the general mapping function according to the invention is described with use of the conventional division in calibration, qualification and synchronization. However, it is the aim of the invention to provide an approach that mixes these three procedures in one single function. According to the invention, a single measurement procedure to establish the parameters has a greater accuracy than establishing the set of parameters in separated methods.

1. Calibration

The calibration step consists essentially of a mapping from the receiver readings to a 1D, 2D or 3D point relative to a coordinate system connected with the non-contact probe. The dimensions of the point are equal to the dimensions of the receiver. For example a camera with a square CCD-array will produce two-dimensional points after calibration. The goal of the calibration is to express the one-, two- or three-dimensional coordinates of a point in terms of its receiver readings.

The "mapping" provides a description of this correspondence. It consists of a function that maps a reading from the receiver domain of all readings to a 1D, 2D or 3D point. Ideally, the mapping function should be able to model various physical effects of the non-contact probe such as the perspective, imperfectness of working principle or heterogeneous reading resolution and sensitivity.

Several methods have already been proposed in the literature that define generic or specialized mapping functions. The simplest method consists of defining one single function that covers the entire mapping area. The form of this function is critical and prior knowledge of the problem is necessary to make an educated choice. The second class of mapping methods is generic; it is able to effectively model any mapping function provided that the number of parameters is sufficiently high. These methods work by a divide-and-conquer approach, dividing the mapping area in smaller area and defining simple shape functions for the local mapping. The local mapping is then aggregated into a global mapping.

In the present invention any general mapping function can be used, as long as the function offers enough detail to model an accurate conversion from reading to point. For the sake of generality, all points here are considered to be three dimensional. One or two dimensional point can be represented by a three dimensional point without any loss of information. The general representation is given below where $P_r$ (resp. $P_{3D}^c$) represents the receiver reading (resp. 3D point), f is the general mapping function $$P_{3D}^c = f(P_r), \qquad (1)$$

With f defined as $$f: D \rightarrow \Re^3. \qquad (2)$$

and $\Re^3$, the three dimensional space and D, the domain of the all possible readings of all receivers:

$$D = \cup_{\forall i} D_i \qquad (3)$$

$$D_i \cap D_j = \emptyset \text{ for } i \neq j \qquad (4)$$

$D_i$, the domain of all possible readings of the $i^{th}$ receiver and this for all receivers. A crucial question concerns the amount of data needed to compute the actual parameters of the mapping function. Unfortunately, there is no definite answer to this question. It depends on the accuracy needed and on the scale of the phenomenon studied.

2. Qualification

Qualification consists of a three-dimensional mapping. The calibration maps the reading onto a point located in the physical space, relative to a coordinate system fixed to the non-contact probe. The exact position of this non-contact probe and the determination of its orientation are the tasks of the qualification. The position and the orientation will be determined relative to a coordinate system fixed to the object to be scanned.

The non-contact probe coordinate system is described by 6 parameters, three translation components and three rotation components. The system can be decoupled into the translation component q of the non-contact probe and in the rotation matrix Q. The relation between the localizer and the object is similarly given by its orientation M and translation m. A three-dimensional point $P_{3D}^q$ relative to the fixed coordinate system is written as $$P_{3D}^q = M*(Q\,P_{3D}^c + q) + m, \quad (5)$$

with $P_{3D}^c$ a three-dimensional point relative to the non-contact probe coordinate system.

In instances where the value of m depends on Pr, the equation may be rewritten as Equation 5.1, which also cover instances when m is independent of Pr.

$$P_{3D}^q = M*(Q\,P_{3D}^c + q) + m(Pr), \quad (5.1)$$

Where m(Pr) is the value of m when m depends on Pr.

In general as the localizer moves the non-contact probe and/or the object in space the relative position and orientation of the probe to the object changes. In other words the rotation matrix M and translation component m both change during movement.

3. Synchronization

During the measurement of an object, the localizer moves and both M and m change continuously, however, the localizer only returns their values at given discrete time steps. Interpolation (linear, parabolic, cubic, or any suitable interpolation scheme (Piegl and Tiller)) are generally used to return a value for intervening time points which can be synchronised with the readings of the receiver. Interpolation of readings from the localizer can be expressed mathematically according to equation (6):

$$M{:}t \to M(t) \text{ and } m{:}t \to m(t) \quad (6)$$

where M(t) and m(t) are continuous functions of the time t defined from the discrete values of M and m.

In regard of the receiver readings, a synchronization function s that returns a time stamp for every receiver reading, is usually implemented i.e.

$$s{:}Pr \to t \text{ where } t = s(Pr). \quad (7)$$

In general this function can be any suitable synchronization function of the art, and which can be implemented by the skilled person. It can be defined based on the receiver design, or by use of a general mapping function such as a non-uniform rational B-spline (NURBS) curve. This function, s, is not defined a priori. It uses a set of parameters that need to be identified, which requires the use of separate, time-consuming procedures.

A special instance of s, for a receiver that obtains readings at a fixed rate, we can define $$t_n = s(Pr) = \text{delta} + n/f, \quad (8)$$

where $t_n$ is the time stamp of the receiver reading n, delta is a phase shift (in seconds) and f is the receiver frequency (in Hz). The variables delta and/or f can be considered as parameters that need to be identified in the synchronization function s.

Synchronization described above allows a time stamp to be associated with receiver readings which are produced by a probe periodically, regularly, or a combination of these. It also allows localizer readings to be determined at any time stamp associated with the receiver readings. During the measurement of an object, therefore, both probe and localizer readings are synchronized, so improving the accuracy of the information provided by both devices Using Equation (6), values of M and m at any time t can be readily determined, and using Equation (7), values of t for every receiver reading, Pr can be calculated. Combining Equations (6) and (7), thus, provides a method to obtain the precise values of M and m for every Pr. When M and Pr are synchronised, we have $$M = M(s(Pr)) \quad (9)$$

It is as aspect of the present invention that the parameters of function s are identified simultaneously with the parameters of calibration and qualification, and not separately.

As described above, the necessary steps to convert individual readings of the receivers into actual three-dimensional coordinates, with (if available) the knowledge of the position and orientation of the probe given by the localizer at discrete time steps, are normally de-coupled. By aggregating these various steps, we can thus express directly a 3D point $P_{3D}^q$ (also known as P herein) in terms of a receiver reading $P_r$ by $$P_{3D}^q = M(t)*(Q(f(P_r)) + q) + m(t), \quad (10)$$

or $$P_{3D}^q = M(s(Pr))*(Q(f(P_r)) + q) + m(s(Pr)), \quad (10.1)$$

where f is the calibration function, Q, q and are the position and orientation of the probe stemming from the qualification; M, m and s are the continuous localiser and receiver time functions. These functions and these symbols have been defined in eqs. (1) to (7). Equations (10) and (10.1) contain the following parameters to be defined in the calibration-qualification-synchronization procedure:

- the function f is a general mapping function with enough parameters to accurately model the transformation from receiver reading to 3D point in the probe space. Such functions are known in the art. If for example a polynomial function is chosen as mapping function, then the parameters are the coefficients. The degree and the type of polynomial are not parameters but constants.

- Depending on the accurate information obtained from the localizer, either three translation components (the position m), or three rotations (the orientation Q), or both are considered as parameters. For example if the localizer is a CMM with accurate information on the position of the probe in the localizer space and the probe performs only parallel movements, the three rotations (the orientation Q) are the only parameters.

- The synchronization function s.

All these parameters can be grouped in a parameter set S, which includes synchronization parameters, and equation (10.1) can be rewritten as:

$$P_{3D}^q = F(P_r, S) \quad (11)$$

With F the compensation function based on a calibration—qualification—synchronization procedure with parameter set S:

$$F:D\to\Re^3 \qquad (12)$$

And D defined as in eqs. (3) and (4).

In another embodiment, the present invention relates to a method of determining calibration, qualification and synchronization parameters, which is based on a generic function, said generic function being a non-uniform rational B-spline function. The present invention relates to a new general procedure or method for determining all these parameters in a single step. In an embodiment the present invention relates to a method of determining a parameter configuration comprising the steps of:

scanning an single artifact; and applying a computational procedure to adjust all said parameters directly and simultaneously using the scanning data.

Said parameter configuration comprises the parameters mentioned above which are required to establish a generic model in which the steps of calibration, qualification and synchronization are integrated.

In one embodiment of the invention, the artifact used for calibration, qualification and synchronization of the non-contact probe is identical to the artifact used for the qualification of probe which is a tactile or contact probe and said artifact is a sphere.

The method of the invention for simultaneous determination of calibration, qualification and synchronization using a single artifact has several key features. Importantly, only one single artifact is used. Also, the exact size, position, or orientation of this artifact is not initially known. Furthermore, all parameters are evaluated concurrently. In addition, the method performs only one scan of the reference object or artifact and very little user interaction is required. Using this method the adjusted parameters are obtained, which can be used in the above-described generic function.

In a preferred embodiment, the present invention relates to a method of determining calibration and qualification parameters comprising the steps of scanning a single artifact;

determining the optimal position, and optionally, the orientation and/or size of said artifact using the scanning data;

evaluating the quality of said parameter configuration via a multidimensional optimization procedure; and determining the best configuration of the parameters.

An example of the procedure is described in more detail as follows: An initial parameter configuration S in equation (11) is chosen. This configuration is used to establish the generic model described above. Subsequently, an artifact is scanned. The data obtained by a scan of this reference object is a series of receiver readings optionally together with the positions and/or orientations of the probe relative to the artifact. When applying the generic model, which was established using the configuration S, to this series of receiver readings a cloud of 3D points is obtained. As neither the exact position, orientation nor size of the reference object are known, using the cloud of 3D points the optimal position and optionally the orientation and/or size of the artifact that matches the 3D points is first determined. Note that calculating the optimal orientation or size of an artifact is optional, depending on the geometry of the object, and whether any dimensions are already known; when a sphere is used, for example, the orientation does not need to be determined, as described below; when the artifact is an object of known dimensions, only the position and orientation of the object need to be determined. Once the position, orientation and size of the artifact have been determined, the cloud of 3D points can be "compared" with the scanned artifact, and then the quality of the parameter configuration (S) is evaluated. Finally, since a cost or a quality can be assigned to each configuration S, a standard multidimensional optimization procedure can be applied to determine the best configuration $S_{best}$.

In the following description, the standard multidimensional optimization procedure is explained in further detail. Designing a proper cost function is crucial in any optimization procedure and it has been the subject of many publications in the prior art. A "good" cost function should represent accurately the model being investigated without being too complex as to prevent any optimization. In other words, a minimum of the cost function should represent an optimal configuration of the parameters while plateau's in the cost function should be avoided to ensure convergence of the iterative algorithm. From a computational point of view, the cost function should also be easy to compute as it needs to be evaluated many times.

A multidimensional optimization procedure of the present invention is disclosed in the following description. In one aspect of the invention, an algorithm starts from an initial configuration $S_{ini}$ and defines it as the current configuration $S_{cur}$. Then, in a loop, the configuration is iteratively adapted, yielding each time a new $S_{cur}$, in an attempt to better match the cloud of 3D points with the artifact shape. The algorithms stops when the accuracy can no longer be improved, i.e. when the cost function is at its minimum.

In a method of the present invention, the evaluation of the cost function consists of two phases. The first phase consists of determining the best position, and optionally size and/or orientation of an artifact using the 3D points obtained with the active configuration $S_{cur}$. Depending of the shape of the artifact a direct computation or an iterative computation is performed.

In the second phase, the distance between the individual 3D points and the artifact are computed and aggregated, using, for example, one or more average square distance, variance, volume, area computation, axis of inertia calculations, or other method known in the art, to give the actual cost of the parameter configuration. In the ideal situation, when all distances are zero, i.e. all points lie perfectly on the artifact, the cost function is zero and the active configuration is optimal. An example of an algorithm is given below:

1. Choose an initial configuration $S_{ini}$
2. Set initial configuration as current configuration $S_{cur}=S_{ini}$
3. Set $S_{best}=S_{cur}$ and the cost $C(S_{best})=\infty$
4. While $C(S_{best})$ is not within the desired accuracy (as set by the user), do the following:
5. Compute the cloud of 3D points from eq. (7), using the receiver readings and $S_{cur}$
6. Evaluate the best position, and optionally, orientation and/or size of the artifact for the computed 3D points
7. Compare the virtual artifact with the 3D points to compute the cost $C(S_{cur})$
8. If $C(S_{cur})<C(S_{best})$, $S_{best}=S_{cur}$.
9. Choose a new $S_{cur}$ keeping fixed the parameters of f2

At the end of the computation, the parameters of $S_{best}$ are those that give the best representation of the artifact.

Step 6 determines the best position and optionally, the orientation and/or size of the artifact, by comparing a cloud of 3D points generated in step 5 with the artifact. In one aspect of the invention, if the artifact is an object of unknown position, dimension(s) and orientation, but its shape is mathematically defined, the best-fit position, dimension(s) and orientation may be derived by iterative fitting the unknown position, dimensions and orientation using the mathematical description of the shape to the cloud of 3-D points. In another aspect of the invention, if the artifact is an irregular object of accurately known dimensions, its position and orientation may be determined by iteratively fitting the best position and orientation of the object dimensions to the cloud of 3D points. The dimensions may be read, for example, from a look-up table. The method can determine the best position, orientation and size of the artifact, for any combination of available object parameters. The iterative fittings of the artifact to the cloud points may be performed by a shaping-matching model comprising any known methods of the art. Possible shapes of the artifact include cylinders, cubes, boxes, spheres, any irregular or regular shape.

For the purpose of illustration, general shape matching with a sphere will be described, although the procedure is non-limiting for the present invention. A sphere can be described by 3 parameters for its center c: $(c_x, c_y, c_z)$, and one parameter for its radius r. For every point p, with parameters $(p_x, p_y, p_z)$, it is then easy to compute its distance d to the sphere as $$d=\|p-c\|_2-r=((p_x-c_x)^2+(p_y-c_y)^2+(p_z-c_z)^2)^{1/2}-r \quad (13)$$

or a pseudo distance $$d'=\|p-c\|_2^2-r^2=(p_x-c_x)^2+(p_y-c_y)^2+(p_z-c_z)^2-r^2 \quad (14)$$

For a given set of parameters (c, r), it is then possible to define a cost function:

$$C_{art}(c,r)=\Sigma d^2, \quad (15)$$

or $$C_{art}(c,r)=\Sigma d'^2, \quad (16)$$

where the sum goes over all points of the receiver(s).

Standard derivation techniques can be used to determine the values of c and r that minimize $C_{art}$. When the cost function $C_{art}$ is non linear, a regular multidimensional optimization procedure can be used to determine the best values of c and r.

The results of step 6 is a virtual artifact whose best position, size and orientation have been calculated (or were partly already known). In step 7, the cloud of 3D points generated in step 5 is compared to said virtual artifact, and a cost of fitting is generated for a set of S parameters. The method used to generate the cost (the cost function, C) can be any known in the art, as already mentioned above. The value of S is adjusted until the cost of fitting is minimized. The minimization procedure can be any known in the art.

Thus, the two cost functions C and $C_{art}$ used in the calibration-qualification procedure are described above. The general cost function C is used to find the parameter configuration for the calibration and qualification while the second function $C_{art}$ is used inside the first to find the best shape.

According to the above example, only the shape of the sphere is needed and not its actual size. As a consequence, the radius r of the sphere is required to be determined by the shape-matching model $C_{art}$. Of course if, for other shapes, additional information is available, such as a size, an aspect ratio, dimensions etc, they can be easily used to reduce the number of parameters required to be determined by the shape-matching model. In the example provided above in which the artifact is a sphere, were the radius to be already known, the problem would be reduced to the determination of the optimal sphere center c—and so there would only be three parameters to determine.

When robust optimization algorithms are used, the initial configuration is of little importance. However, when the cost function contains many local minima, providing an initial configuration close to the optimal, but unknown, configuration is desirable. With the model according to the present invention, it is also possible to automate this step. Indeed, the model according to the present invention contains two loosely connected entities, namely, the calibration and the qualification. In order to the find an initial good configuration, one of both entities is fixed and the other one is solved.

More precisely, when qualification is not required and hence neglected in the calculation, only the calibration is investigated. When only a calibration is performed, values of Q and m according to equation 10.1 should be known and are fixed in the calculation.

With a fixed calibration, the optimization of, at most, 6 parameters of the qualification can be performed in a straightforward manner using a method of the present invention. When only a qualification is performed, the value of F should be known and fixed in the calculation.

When calibration, qualification and synchronization calculations are performed separately as described in the preceding paragraphs, the values obtained by one calculation may be used as the fixed, known parameter in the other calculation. For example, a qualification-only optimization will produce values of Q and q; the values of Q and q so calculated can be used as the fixed values in the calibration-only optimization and in the synchronization only operation. Performing several iterations of separate calibration, qualification and synchronization calculations wherein the parameters obtained from one calculation are used in the other calculation, results in an initial configuration parameter set that is close to the optimal configuration achieved by performing calibration and qualification simultaneously.

With certain choices of fixed parameter subset, the complexity of the optimization problem reduces significantly. For example, if f1 contains the linear parameters of the calibration, the optimization becomes a linear problem and can be solved directly without the need of an iterative procedure. Similarly, if f1 is defined as a continuous function, its derivative can be analytically estimated and hence, faster and more robust optimization techniques may be employed.

Using presently known methods, the synchronization uses qualification and calibration, and must then be performed after these steps. There are two possible choices using the methods in the art:

1. Calibration and qualification are performed with a continuous motion of the localizer without synchronization in which case the results are thus not accurate.
2. Calibration and qualification are performed with discrete motion of the localizer, i.e. one must ensure that the localizer is absolutely still for every receiver readings. This is a time consuming procedure.

Hence, using methods of the art either time or accuracy are lost. By simultaneously determining parameters of synchronization with calibration and qualification, these problems are overcome.

The method presented herein allows an unskilled operator to perform a simultaneous calibration, qualification and synchronization of a point cloud generator. The quality of said calibration, qualification and synchronization are independent of the skill of the operator, in contrast to the present methods of the art, which are technically demanding and require a high level of skill and experience.

The method presented herein allows a simultaneous calibration, qualification and synchronization of a point cloud generator within 5 minutes of the generation of the cloud point. The method presented herein allows an improved simultaneous calibration, qualification and synchronization of a point cloud generator within 10, 15, 20, 25, 30, 35, 40, 45, 50, 55, 60, 70, 80, 90, 100, 120, 140, 160, 180, 200, 250, 300, 350, 400, 450, or 500 minutes of the generation of the cloud point. The speed of the method is achieved because no manual interventions are required; the method is automatic.

The method presented herein allows a simultaneous calibration, qualification and synchronization of a point cloud generator without manual intervention, once the first scan has been instructed, in contrast to the present methods of the art, which requires extensive manual interventions and skill to adjust components of the point cloud generator.

In one embodiment of the invention, the minimisation algorithm given in FIG. 1 is used. The minimization algorithm uses a Monte-Carlo method where the current calibration, qualifications and synchronization are randomly perturbed and accepted if the resulting set of points is closer to the artifact (see Z. Michalewicz, "Modern Heuristics" for a survey of Monte-Carlo method). The calibration is performed by means of a non-uniform rational B-spline (NURBS) curve or surface depending on the dimension of the receiver. The algorithm uses an order two NURBS with uniform knot vector (see Piegl and Tiller, "The NURBS Book"). The numbers of knots and control points depend on the desired accuracy of the calibration. The qualification is defined as a 4×4 matrix with 6 degrees of freedom.

In another embodiment, the present invention relates to the use of a single artifact for performing the calibration, qualification and synchronization procedure according to the method of the invention.

In another embodiment, the present invention relates to a computer program stored on a computer readable medium wherein the steps of the method according to the invention are performed. Another embodiment of the invention concerns a computer adapted and programmed to carry out the computer program according to the invention.

Moreover, the present invention also relates to a non-contact probe configured to perform a method of the invention. This non-contact probe is consequently capable of performing at least 1 and preferably the 2 steps of calibration, qualification and synchronization in a single operation. After these steps have been performed the non-contact probe is ready for industrial use by the end-user, until it is dismounted from the localizer or until its position or orientation is changed with respect to the localizer.

The present invention also provides for a non-contact device comprising a non-contact probe according to the invention, which is mounted on a localizer, and an artifact.

The invention claimed is:

1. A method for the calibration, qualification and synchronization of a point cloud generator, said point cloud generator comprising a non-contact probe on a localizer, comprising determining the transformation of an electrical reading of the receivers in said non-contact probe in point coordinates relative to said probe and identifying the position and orientation of the said non-contact probe in the measuring volume of the said localizer, thereby determining calibration, qualification and synchronization parameters simultaneously.

2. A method according to claim 1 whereby calibration, qualification and synchronization are performed using the same artifact.

3. A method according to claim 2, whereby said artifact is a physical object susceptible to point cloud generation, whose outer shape and/or part thereof is definable using a mathematical function and/or look-up tables.

4. A method according to claim 2, whereby said artifact is a sphere, cylinder or box.

5. A method according to claim 2, whereby said artifact is a sphere of unknown diameter.

6. A method according to claim 2, whereby said artifact has unknown dimensions prior to the execution of said method.

7. A method according to claim 2, whereby said artifact has unknown position with respect to said localizer prior to the execution of said method.

8. A method according to claim 1, whereby said method is performed without manual intervention.

9. A method according to claim 1, whereby said method is executed at a user's site.

10. A method according to claim 2, comprising the steps of:
    a) scanning said artifact using said point cloud generator,
    b) calculating cloud points, P, using parameters relating to calibration, qualification and synchronization,
    c) calculating the position and optionally the orientation and/or size of said artifact using P calculated in step b) and knowledge of the arteface according to a mathematical function and/or look-up tables which define said artifact,
    d) comparing the values of P, with those calculated for the artifact derived from step c),
    e) adjusting parameters relating to calibration, qualification and synchronization, and
    f) repeating steps b) to e) until parameters relating to calibration, qualification synchronization are obtained which provide the closest comparison according to step d).

11. A method according to claim 10, wherein steps b) to f) comprise:
    b) calculating points according to [2]:

$$P=F(Pr, S) \qquad [2]:$$

wherein Pr is a reading of a receiver of the non-contact probe,
    P is a point, calculated from Pr, relative to a fixed coordinate system,
    S is a parameter set describing qualification, calibration and synchronization, and
    F is a compensation function to convert a receiver reading in a 3D point relative to a fixed coordinate system, said compensation function being applied to Pr using parameter set S,
    c) calculating the position and optionally the orientation and/or size of said artifact using the values of P obtained in step b),
    d) comparing the values of P, with those calculated for the artifact derived from step c),
    e) adjusting S, and
    f) repeating steps b) to e) until value of S is obtained which provides the closest comparison according to step d).

12. A method according to claim 10 wherein step c) comprises:

g) comparing the points P obtained in step b) to those expected of said artifact according to a mathematical function and/or look-up tables which define said artifact, h) adjusting one or more of the values corresponding to the position and optionally the orientation and/or size of said artifact, and i) repeating steps g) and h) until values corresponding to the position, and if calculated orientation and/or size are obtained which provide the closest comparison according to step g).

13. A method according to claim 10 wherein the values calculated for the artifact as mentioned in step d) are derived from a mathematical function and/or look-up tables which define said artifact, the values corresponding to the position, and if calculated orientation and/or size as obtained in step c).

14. A method according to claim 10, wherein the comparison performed in step d) comprises one or more average square distance, variance, volume, area and/or axis of inertia calculations.

15. A method according to claim 11 whereby step b) is based on the function [1]

$$P=M(s(Pr))*(Q(f(Pr))+q)+m(s(Pr)) \qquad [1]$$

where

Pr is a reading of a receiver of the non-contact probe,

P is a cloud point, calculated from Pr, relative to a fixed coordinate system, f is a general mapping function, that maps receiver readings to 1D, 2D or 3D point coordinates, relative to a coordinate frame fixed to the non-contact probe, Q, q are the orientation, position of the non-contact probe relative to the localizer, M, m are the orientation and position of the localizer relative to a fixed coordinate frame for a given value of Pr, s is the time stamp for a given value of Pr; all three with respect to a fixed coordinate frame; none or one or more considered as known parameters.

16. A method according to claim 15 wherein f is a non-uniform rational B-spline function.

17. A method according to claim 15 wherein s is a non-uniform rational B-spline function.

18. A method to allow an unskilled operator to perform a calibration, qualification and synchronization of a point cloud generator, using a method defined in claim 1.

19. A method for performing a simultaneous calibration, qualification and synchronization of a point cloud generator within 5 minutes of generating the cloud point, using a method defined in claim 1.

20. A method for performing a simultaneous calibration, qualification and synchronization of a point cloud generator without manual intervention, using a method defined in claim 1.

21. Use of a single artifact for performing the calibration, qualification and synchronization procedure according to the method of claim 1.

22. A computer program stored on a computer readable medium, suitable for performing a method according to claim 1.

23. Computer comprising a computer readable medium adapted and programmed to carry out the computer program according to claim 22.

24. A non-contact probe configured to perform a method of claim 1.

25. A non-contact device comprising an artifact and a non-contact probe according to claim 24 mounted on a localizer.

26. A method for the simultaneous calibration, qualification and synchronization of a point cloud generator, said point cloud generator comprising a two-dimensional line laser scanner mounted on a 3D co-ordinate measuring machine, comprising:

j) scanning a sphere using said point cloud generator, k) calculating points according to function [2]

$$P=F(Pr, S) \qquad [2]$$

wherein Pr is a reading of a receiver of the two-dimensional line laser scanner, P is a point, calculated from Pr, relative to a fixed coordinate system, F is a compensation function based on f, Q, q, S, M and m, said compensation function being applied to Pr using parameter set S, Q, q is the orientation and position of the line laser scanner relative to the 3D co-ordinate measuring machine; s is the time stamp for a given value of Pr; f is a general mapping function, that mares receiver readings to 1D, 2D or 3D point co-ordinates, relative to a co-ordinate frame fixed to the line laser scanner; M, m is the orientation position of the 3D co-ordinate measuring machine relative to a fixed frame for a given value of Pr; all values with respect to a fixed coordinate frame and none, one or more, or all values considered as known parameters, l) comparing the points P obtained in step k) to those expected of said sphere according to a mathematical function defining said sphere, m) adjusting one or more of the values corresponding to the position and size of said sphere, n) repeating steps l) and m) until values corresponding to the position and size are obtained which provide the closest comparison according to step l), o) comparing the values of P, with those calculated for the sphere, the latter obtained from mathematical function which defines said sphere, and the values corresponding to its position and size as obtained in step n).

p) adjusting S, and q) repeating steps k) to n) until value of S is obtained which provides the closest comparison according to step o).

* * * * *